United States Patent [19]

Tarassoff et al.

[11] 4,003,814
[45] Jan. 18, 1977

[54] APPARATUS FOR THE CONTINUOUS MEASUREMENT OF THE OXYGEN CONTENT OF MOLTEN COPPER OR ALLOYS THEREOF

[75] Inventors: Peter Tarassoff, Dollard des Ormeaux; Tadeusz R. Kowalski, Ville d'Anjou; Meguru Nagamori, Ste. Foy, all of Canada

[73] Assignee: Noranda Mines Limited, Toronto, Canada

[22] Filed: July 21, 1975

[21] Appl. No.: 597,760

[30] Foreign Application Priority Data

Aug. 2, 1974 Canada ............................ 206219

[52] U.S. Cl. ........................... 204/195 S; 324/30 R
[51] Int. Cl.² ..................................... G01N 27/46
[58] Field of Search .......................... 204/15, 195 S

[56] References Cited

UNITED STATES PATENTS

| | | | |
|---|---|---|---|
| 3,642,599 | 2/1972 | Franz | 204/195 S |
| 3,661,749 | 5/1972 | Richardson | 204/195 S |
| 3,784,459 | 1/1974 | Jackson | 204/195 S |
| 3,864,232 | 2/1975 | Handman et al. | 204/195 S |

OTHER PUBLICATIONS

Kinzel et al., "The Alloys of Iron and Chromium", 1940, p. 369.

Primary Examiner—T. Tung
Attorney, Agent, or Firm—Finnegan, Henderson, Farabow & Garrett

[57] ABSTRACT

An apparatus for the continuous measurement of the oxygen content of molten copper and alloys thereof is disclosed. The apparatus comprises an austenitic stainless steel tube possessing a large heat capacity and capable of withstanding the operative conditions of molten copper and alloys thereof, a closed end tube of solid electrolyte inserted inside the stainless steel tube and projecting from the end of the stainless steel tube a distance at least equal to the diameter of the solid electrolyte tube, a relatively thick layer of fine grained alumina cement inserted between the stainless steel tube and the solid electrolyte tube for cementing the stainless steel tube to the solid electrolyte tube, and threads on the inside of the stainless steel tube for permitting the alumina cement to stick to the stainless steel tube. A first electrical connection is provided with the inside of the solid electrolyte tube at the bottom thereof wherein a predetermined reference oxygen potential is maintained, and a melt contact is immersed in the molten copper or alloy thereof for providing a second electrical connection with the outside of the solid electrolyte so as to measure the difference of potential between the two faces of the solid electrolyte as an indication of the oxygen content of the molten copper or alloy thereof.

12 Claims, 1 Drawing Figure

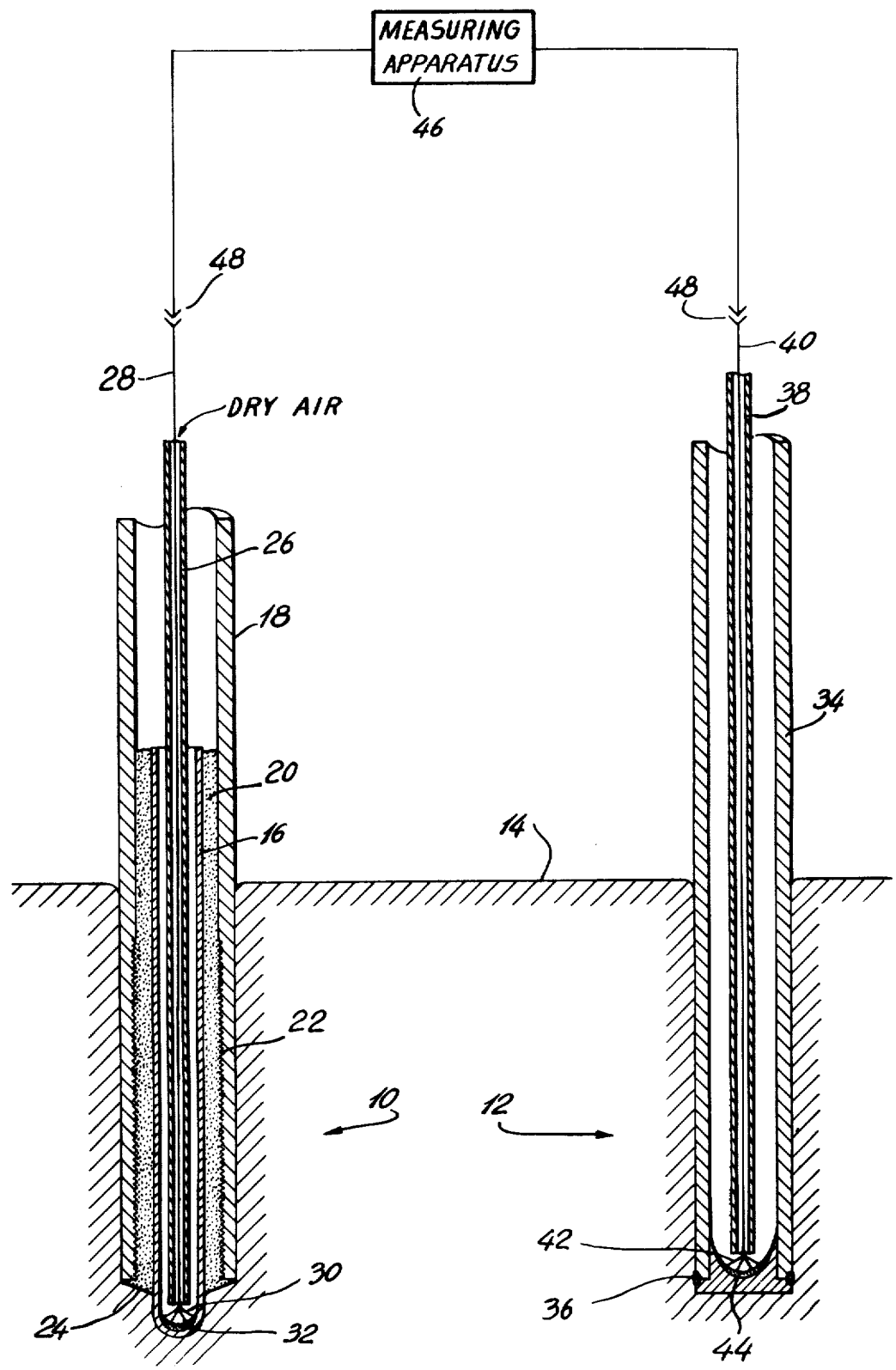

APPARATUS FOR THE CONTINUOUS MEASUREMENT OF THE OXYGEN CONTENT OF MOLTEN COPPER OR ALLOYS THEREOF

This invention relates to an apparatus for the continuous measurement of the oxygen content of molten copper and copper alloys. More particularly, the invention is directed to a probe for continuously measuring the oxygen content of molten copper and copper alloys in a launder, wirebar ladle or other vessel, by means of a galvanic, or electromotive cell employing a solid electrolyte.

Oxygen probes based on galvanic cells employing solid oxide electrolytes have gained wide industrial use for the determination of oxygen dissolved in liquid metals. The galvanic cell in an oxygen probe for copper may be represented as, Melt Contact, $O_2$ |Solid Oxide Electrolyte |$\underline{O}$ (in Cu), Reference Electrode Contact (1)

where O is oxygen dissolved in the liquid copper, and $O_2$ is a fixed partial pressure of oxygen at the reference electrode. The most commonly used electrolytes are the Group IVB oxides $ZrO_2$ and $ThO_2$, containing either CaO, MgO or $Y_2O_3$ in solid solution. These solid solutions contain anion vacancies and conduct current exclusively by oxygen ion migration over a wide range of temperatures and oxygen partial pressures. A differential oxygen pressure imposed across the solid electrolyte in cell (1) causes a cell potential or emf $$E = -\frac{RT}{2F} \ln a_0 + \frac{RT}{4F} \ln p_{o_2} \qquad (2)$$

where $E$ is the emf ($mV$), $T$ is the absolute temperature (°K), R is the gas constant (1.987 cal./mol °K), F is the Faraday constant (23.06 cal./mV °K), $a_0$ is the activity of oxygen dissolved in the liquid copper, and $P_{o_2}$ is the reference partial pressure of oxygen (atm.). The reference partial pressure may be provided by a gas, such as air, or a metal/metal oxide mixture such as Ni/NiO.

To be suitable for industrial use, an oxygen probe must, among other requirements meet the following criteria:

a. High resistance to thermal shock;
b. High resistance to chemical attack by molten metal and any slag thereon; and
c. High resistance to mechanical shock and flame impingement.

In one class of probes, as illustrated by Canadian Pat. No. 871,239 to Pargeter and Canadian Pat. No. 858,042 to Hans et al., the problem of thermal shock is overcome by using a very small electrolyte pellet which is mechanically sealed into an insulating tube of fused silica, or the like, and heats up rapidly and uniformly. This type of probe can withstand the molten metal for an interval just sufficient to obtain an e.m.f. reading representative of the oxygen content of the metal according to equation (2) before the cell portion of the probe is destroyed by the melt. The expendable portion must be replaced before another measurement can be made. Obviously, this is a serious disadvantage where it is desired to control the oxygen content of a flowing stream of metal as in the casting of wirebar copper. The large number of measurements required for effective control makes the use of expendable one-reading probes uneconomic.

In a second class of oxygen probe, intended for continuous immersion in a melt, the solid electrolyte may be in the form of a closed-end tube or it may be an integral part of a ceramic tube. Such tubes must be protected from thermal and mechanical shock, and from chemical attack particularly at the molten metal-slag or molten metal-gas interface. Richardson in Canadian Pat. No. 839,938 encloses the electrolyte tube in a refractory metal or cermet sheath, which being conductive, also acts as the melt contact. It is very difficult to obtain a tight seal between a ceramic tube and a metal or cermet sheath, because these elements have very different thermal coefficients of expansion. In order to counteract thermal shock during immersion, Richardson places the probe in a block of solid copper; the probe then heats up slowly as the copper melts. This construction of the probe is complex and such probes are therefore expensive.

The object of the present invention is to provide an apparatus for the continuous measurement of oxygen in molten copper and alloys thereof which satisfies the above-mentioned requirements and, at the same time, is very simple in construction and less costly than the existing apparatus.

The apparatus, in accordance with the present invention, comprises an austenitic stainless steel tube possessing a large heat capacity and capable of withstanding the operative conditions of the molten copper and alloys thereof, a closed end tube of solid electrolyte inserted inside the stainless steel tube and projecting therefrom a distance at least equal to the diameter of the solid electrolyte tube, a fine grained alumina cement inserted between the stainless steel tube and the solid electrolyte tube for cementing the stainless steel tube to the solid electrolyte tube, and threads on the inside of the stainless steel tube for permitting the alumina cement to stick to the stainless steel tube. A first electrical connection is provided with the inside of the solid electrolyte tube at the bottom thereof wherein a predetermined reference oxygen potential is maintained, and a melt contact is immersed in the molten copper or alloy thereof for providing a second electrical connection with the other side of the solid electrolyte tube so as to permit measurement of the difference of potential between the two faces of the solid electrolyte as an indication of the oxygen content of molten copper or alloy thereof.

The outside diameter of the solid electrolyte tube may vary between ¼ to ½ of an inch, the inside diameter between 3/16 to 7/16 of an inch and its length between 2 and 8 inches, with the preferred dimension being ⅜ of an inch outside diameter, 5/16 of an inch inside diameter and a length of 6 inches. The stainless steel tube may have an inside diameter varying between ½ and ⅝ of an inch when using a solid electrolyte tube having an outside diameter of ⅜ of an inch. Of course, the inside diameter of the stainless steel tube will vary depending on the outside diameter of the solid electrolyte tube but should be such as to provide a relatively thick layer of cement between the solid electrolyte tube and the stainless steel tube. The thickness of the stainless steel tube may vary between 1/16 to ⅛ of an inch. The length of the stainless steel tube should be longer than the one of the solid electrolyte tube. In a preferred embodiment of the invention, the stainless steel tube is 17 inches long.

The problem of thermal shock is overcome by using a stainless steel tube with a large heat capacity, which together with the heat capacity of the relatively thick layer of cement between the stainless steel tube and the electrolyte tube impart a large heat capacity to the probe. The solid electrolyte tube is therefore shielded from thermal shock.

In the preferred embodiment of the invention, the reference oxygen potential is provided by clean air admitted into the solid electrolyte tube through an alumina refractory tube which is inserted inside the solid electrolyte tube. Electrical contact with the reference side of the solid electrolyte tube is made with a platinum wire inserted in the alumina refractory tube. The platinum wire is connected to the bottom of the solid electrolyte tube by a "spider" of platinum wire, and sponge platinum obtained by decomposing chloroplatinic acid in situ.

In cementing the probe, the closed-end solid electrolyte tube should project a distance equal to its diameter beyond a collar forming a continuation of the cement in the annular space between the electrolyte tube and the stainless steel tube and bounded by a surface extending at about 45° from the outside periphery of the stainless steel tube to the solid electrolyte tube.

In the preferred embodiment of the invention, the means for establishing a second electrical connection with the other side of the electrolyte tube comprises an alumina refractory tube inserted inside a stainless steel tube which is closed at the end thereof immersed in the melt, a platinum wire inserted inside such alumina refractory tube and connected to the bottom of the stainless steel tube by a spider of platinum wire, and sponge platinum obtained by decomposing chloroplatinic acid in situ. The stainless steel tube could also conveniently serve as a thermocouple protection tube.

The invention will now be disclosed, by way of example, with reference to a preferred embodiment illustrated in the accompanying drawing.

Referring to the drawing, there is shown a measuring probe 10 and a contact probe 12 immersed into a bath 14 of molten copper or alloy thereof. The measuring probe 10 comprises a solid electrolyte tube 16 cemented inside an austenitic stainless steel tube 18 by means of a relatively thick layer of cement 20. The solid electrolyte tube 16 consists preferably of an impervious ultra-high density slip cast closed end tube of magnesia stabilized zirconia such as the one sold by Zirconium Corporation of America under Zircoa group No. 32-0518, product No. 085. The solid elctrolyte tube 16 may also be made of thorium oxide ($ThO_2$) as mentioned previously. Both zirconia ($ZrO_2$) or thorium oxide ($ThO_2$) tubes may be stabilized with calcium oxide, magnesium oxide or yttrium oxide. The stainless steel tube 18 must have a large heat capacity and be capable of withstanding the operative condition of the melt. Such stainless steel tube must be of the austenitic type, and preferably the one known in the trade as 310 stainless steel and containing 24–26% Cu, 19–22% Ni, and the rest iron. The one known in the trade as 316 stainless steel and containing about 18% Cu, 10% Ni and the rest iron, may also be used although it has a shorter useful life in the present application.

The cement 20 is a fine-grained alumina cement or mortar containing at least 99% $Al_2O_3$. One example of such a cement is Alumina Mortar MA 176 available from Norton Co. of Canada. The inside of the stainless steel tube 18 is threaded, as illustrated at 22 for insuring sticking of the cement to the inside wall of the stainless steel tube. In cementing the probe, the closed-end solid electrolyte tube should project a distance equal to its diameter beyond a collar 24 forming a continuation of the cement in the annular space between the electrolyte tube and the stainless steel tube and bounded by a surface extending at approximately 45° from the outside periphery of the stainless steel tube to the solid electrolyte tube. The solid electrolyte tube projects a distance at least equal to its diameter beyond the collar 24 to leave out a substantial surface of the end of the electrolyte tube in contact with the melt. After cementing, the wet alumina cement is dried below 100°–110°C, followed by slow cooling to room temperature. For proper operation of the probe, the cement seal must be impervious to gas and liquid molten copper or copper alloy. A particularly reliable seal is produced if, after the initial cementing and heat setting, a water-rich alumina cement is applied to the outside of the seal with a negative pressure inside the measuring probe. The upper part of the solid electrolyte tube may be centered inside the stainless steel tube with any convenient refractory ring imbedded in the cement.

In the preferred embodiment illustrated in the drawing, the reference oxygen potential is provided by clean dry air admitted into the probe through an alumina refractory tube 26 which extends short of the bottom of the solid electrolyte tube. It is to be understood, however, that the required reference potential may be provided by using a metal/metal oxide mixture such as Ni/NiO. Electrical contact to the reference side of this solid electrolyte is made with a platinum wire 28 inserted in the alumina refractory tube 26. The platinum wire is connected to the bottom of the solid electrolyte tube by a "spider" 30 of platinum wire, and sponge platinum 32 obtained by decomposing chloroplatinic acid in situ. It is to be understood that other means of making a connection with the bottom of the solid electrolyte tube are also envisaged.

The contact probe 12 consists of a stainless steel tube 34 capable of withstanding the operative conditions of the melt and is preferably of the austenitic type. It is closed by a plug 36 of the same material welded to the tube although it could obviously be an integral closed-end tube. An alumina refractory tube 38 similar to alumina tube 26 of the measuring probe is inserted inside the stainless steel tube 34 and a platinum wire 40 is connected to the plug 36 at the bottom of the stainless steel tube 334 by means of a spider 42 of platinum wire and sponge platinum 44 obtained by decomposing chloroplatinic acid in situ as for the reference electrode. Of course, other means of providing electrical contact with the melt are also envisaged.

The measuring and contact probes 10 and 12 are each supported by any suitable holder and the holders supported by any convenient assembly to permit dipping of the probes in the melt for taking measurements and withdrawing the probes from the melt. Such an assembly is well known in the art and it is not believed that the description thereof is necessary. To prevent oxygen of the surrounding air from influencing the reading of the oxygen probe, a layer of charcoal having a thickness of about 2 inches may be placed on the surface of the molten bath.

Clean dry air is fed to the inside of the alumina tube 26 by means of an extension tube (not shown) mounted in the upper side of the measuring probe.

The probe e.m.f. is measured by an apparatus 46 of known construction connected to platinum wires 28 and 40 by means of a suitable connected such as illustrated diagramatically at 48. Typically, the measuring apparatus comprises a probe signal conditioner (pre-amplifier and filter), a high impedance volt meter with a r.f. line filter and a recorder to record the e.m.f. or with the addition of a logarithmic converter, the oxygen content of the copper.

While elaborate heating and cooling of the probe is not absolutely necessary, the useful life of the measuring probe is materially extended if it is maintained about 2 inches above the molten metal bath for about 25 minutes prior to dipping. Similarly, satisfactory slow cooling may be obtained by maintaining the measuring probe 2 inches above the molten metal bath for about 10 minutes after withdrawing the probe from the melt.

The above disclosed measuring probe has been found to have a mean useful life of about 75 hours made up, in the average, of four dips of between 15-25 hours. It has also been found that the stainless steel tube itself has a useful life of 500 hours and more and can be reused several times after replacement of the solid electrolyte tube.

In addition, a comparison of the oxygen levels determined by various fusion analyses of plural copper samples during the cast was made with the corresponding probe readings at the time of sampling and found to be in satisfactory agreement therewith as illustrated in the following Table:

| Samples | Oxygen Content in ppm | |
|---|---|---|
| | Probe | Vacuum Fusion |
| 1 | 70 | 70 |
| 2 | 68 | 69 |
| 3 | 65 | 65 |
| 4 | 64 | 70 |
| 5 | 62 | 65 |
| 6 | 100 | 110 |
| 7 | 91 | 95 |
| 8 | 100 | 120 |
| 9 | 109 | 120 |

What is claimed is:
1. An apparatus for the continuous measurement of the oxygen content of copper and copper alloys comprising:
   a. an austenitic stainless steel tube possessing a large heat capacity and capable of withstanding the operative conditions of the molten copper or alloy thereof;
   b. a closed end tube of solid electrolyte inserted inside the stainless steel tube and projecting therefrom a distance at least equal to the diameter of the solid electrolyte tube;
   c. a fine grained alumina cement inserted between the stainless steel tube and the solid electrolyte tube for cementing the stainless steel tube to the solid electrolyte tube;
   d. means on the inside of stainless steel tube for promoting adhesion of the alumina cement to the stainless steel tube;
   e. means for providing a first electrical connection with the inside of the solid electrolyte tube at the bottom thereof wherein a predetermined reference oxygen potential is maintained; and
   f. a melt contact immersed in the molten copper or copper alloy for providing a second electrical connection with the outside of the solid electrolyte as an indication of the oxygen content of the molten copper or copper alloy.

2. An apparatus as defined in claim 1, wherein the solid electrolyte is selected from the group consisting of $ZrO_2$ and $ThO_2$ stabilized with a metal oxide selected from the group consisting of CaO, MgO and $Y_2O_3$ in solid solution.

3. An apparatus as defined in claim 1, further comprising an alumina refractory tube inserted inside the electrolyte tube, and wherein the reference oxygen potential is provided by a gas fed inside said alumina refractory tube and directed toward the bottom of the solid electrolyte tube.

4. An apparatus as defined in claim 3, wherein the gas is air.

5. An apparatus as defined in claim 3, wherein the means for providing a first electrical connection with the inside of the solid electrolyte tube comprises a platinum wire inserted inside said refractory tube, a spider of platinum wire connected to said platinum wire and sponge platinum located at the bottom of the solid electrolyte tube and into which the spider of platinum wire is inserted, said sponge platinum being obtained by decomposing chloroplatinic acid in situ.

6. An apparatus as defined in claim 1, wherein the reference oxygen potential is provided by a metal/metal oxide mixture.

7. An apparatus as defined in claim 6, wherein the metal/metal oxide mixture is Ni/NiO.

8. An apparatus as defined in claim 1, wherein the closed-end solid electrolyte tube has an outside diameter of about ⅜ of an inch and an inside diameter of about 5/16 of an inch and wherein the austenitic stainless steel tube has an inside diameter varying between ½ to ⅝ of an inch and a wall thickness varying from 1/16 to ⅛ of an inch.

9. An apparatus as defined in claim 1, wherein a collar is formed as a continuation of the cement in the annular space between the solid electrolyte tube and the stainless steel tube and wherein the solid electrolyte tube projects a distance beyond the end of said collar.

10. An apparatus as defined in claim 9, wherein the collar is bounded by a surface extending at about 45° from the outside periphery of the stainless steel tube to the electrolyte tube.

11. An apparatus as defined in claim 1, wherein the melt contact consists of an austenitic stainless steel tube closed by a plug of the same material and welded to the end of the tube, and further comprising means for establishing electrical contact with said plug.

12. An apparatus as defined in claim 11, wherein said means for establishing electrical contact with the plug comprises an alumina refractory tube inserted inside the stainless steel tube, a platinum wire inserted inside said refractory tube, a spider of platinum wire connected to said platinum wire, and sponge platinum deposited at the bottom of the stainless steel tube and into which said spider of platinum wire is inserted, said sponge platinum being obtained by decomposing chloroplatinic acid in situ.

* * * * *